(12) United States Patent
Bokermann et al.

(10) Patent No.: US 9,856,152 B2
(45) Date of Patent: Jan. 2, 2018

(54) CONTROL DEVICE FOR A UV-DISINFECTING SYSTEM WITH BROADBAND UV EMITTERS

(75) Inventors: Christian Bokermann, Enger (DE); Sven Kaemmerer, Bad Salzuflen (DE)

(73) Assignee: XYLEM IP HOLDINGS LLC, White Plains, NY (US)

(*) Notice: Subject to any disclaimer, the term of this patent is extended or adjusted under 35 U.S.C. 154(b) by 669 days.

(21) Appl. No.: 14/118,739

(22) PCT Filed: May 16, 2012

(86) PCT No.: PCT/EP2012/002109
§ 371 (c)(1),
(2), (4) Date: Nov. 19, 2013

(87) PCT Pub. No.: WO2012/159719
PCT Pub. Date: Nov. 29, 2012

(65) Prior Publication Data
US 2014/0116961 A1    May 1, 2014

(30) Foreign Application Priority Data
May 20, 2011    (DE) .................. 10 2011 102 687

(51) Int. Cl.
*C02F 1/32*        (2006.01)
*C02F 1/00*        (2006.01)
(Continued)

(52) U.S. Cl.
CPC .................. *C02F 1/32* (2013.01); *A61L 2/10* (2013.01); *A61L 2/24* (2013.01); *A61L 9/20* (2013.01);
(Continued)

(58) Field of Classification Search
CPC ..... A61L 2/10; A61L 2/24; A61L 9/20; A61L 2209/11; B01D 53/007; B01D 53/32;
(Continued)

(56) References Cited

U.S. PATENT DOCUMENTS 5,093,576 A * 3/1992 Edmond ............... H01L 31/103
                                             250/370.01
6,057,917 A    5/2000 Petersen et al.
(Continued)

FOREIGN PATENT DOCUMENTS

| DE | 20 2004 012 686 | 11/2004 |
|----|-----------------|---------|
| DE | 10 2008 051 239 | 4/2010 |
| WO | WO 01/92839 A2  | 12/2001 |

OTHER PUBLICATIONS

Giese et al. (Sensitivity of microorganisms to different wavelengths of UV light: Implications on Modeling of Medium Pressure UV Systems, Water Research, v. 34: 15 (Aug. 21, 2000), pp. 4007-4013).*
(Continued)

*Primary Examiner* — Dirk Bass
*Assistant Examiner* — Hayden Brewster
(74) *Attorney, Agent, or Firm* — RatnerPrestia

(57) ABSTRACT

A device for monitoring and controlling water disinfecting systems having at least one broadband UV emitter arranged in a channel, wherein the device has at least one sensor, which is arranged in the water at a distance from the broadband UV emitter, and wherein the sensor is connected to a control unit, which is set up to control the output of the broadband UV emitter or the volumetric flow of water through the channel, wherein the sensor has a maximum sensitivity to UV radiation in a wavelength range between 200 nm and 240 nm.

11 Claims, 4 Drawing Sheets

(51) Int. Cl.
*A61L 2/10* (2006.01)
*A61L 2/24* (2006.01)
*A61L 9/20* (2006.01)
*H05B 41/36* (2006.01)
*G01J 1/42* (2006.01)
*G01N 21/01* (2006.01)

(52) U.S. Cl.
CPC ............. C02F 1/008 (2013.01); C02F 1/325 (2013.01); H05B 41/36 (2013.01); *A61L 2209/11* (2013.01); *C02F 2201/326* (2013.01); *C02F 2201/3225* (2013.01); *C02F 2209/40* (2013.01); *C02F 2303/04* (2013.01)

(58) Field of Classification Search
CPC ....... B01J 8/02; B01J 9/00; B01J 19/08; B01J 19/087; B01J 19/088; B01J 19/10; B01J 19/12; B01J 19/123; B01J 19/126; B01J 2219/0852; B01J 2219/0894
USPC ......... 210/748.1, 748.11; 250/373, 431, 432, 250/432 R, 435, 436, 455.11; 340/600; 356/43, 47, 50, 213
See application file for complete search history.

(56) References Cited

U.S. PATENT DOCUMENTS

| | | |
|---|---|---|
| 6,429,438 B1 | 8/2002 | Smestad |
| 2004/0061069 A1* | 4/2004 | Schaible .................. A61L 2/10 250/432 R |
| 2004/0200975 A1 | 10/2004 | Brown et al. |
| 2009/0250626 A1* | 10/2009 | Schlesser .............. A61L 2/0011 250/455.11 |
| 2010/0090840 A1 | 4/2010 | Schreiner |

OTHER PUBLICATIONS

International Search Report, dated Jul. 31, 2012, corresponding to International Application No. PCT/EP2012/002109, filed May 16, 2012.

International Preliminary Report on Patentability, dated Nov. 20, 2013, corresponding to International Application No. PCT/EP2012/002109, filed May 16, 2012.

\* cited by examiner

Figure 4.40 Spectral irradiance of Type 1MP lamp #10 as a function of location along the lamp length and around the circumference (C1 - top, C2 - bottom)

CONTROL DEVICE FOR A UV-DISINFECTING SYSTEM WITH BROADBAND UV EMITTERS

CROSS-REFERENCE TO RELATED APPLICATIONS

This application is a U.S. National Phase of PCT Application No. PCT/EP2012/002109, filed May 16, 2012, which claims priority to German Patent Application No. 102011102687.1, filed May 20, 2011, each of which is incorporated by reference herein in its entirety.

FIELD OF THE INVENTION

The present invention relates to a device and a method for controlling UV disinfecting systems in which broadband UV emitters are used. The method as per the invention is designed to achieve control that is as precise as possible of the performance of the disinfecting system, on the one hand to provide the required disinfection performance safely and also to avoid unnecessarily high energy consumption.

BACKGROUND OF THE INVENTION

The germicidal, disinfecting effect of UV radiation has been known for a long time. UV lamps have been used for several decades for disinfecting drinking water and wastewater, in air conditioning systems, sumps and for disinfecting work areas in biological laboratories. UV radiation is produced when disinfecting water and is released into the water thus reaching germs (viruses, bacteria, protozoa). The germicidal effect of the UV radiation is dependent here on the wavelength and on the type of microorganisms that are to be inactivated.

Ultraviolet radiation or ultraviolet light is described as the wavelength range of the electromagnetic radiation, which is between visible light and x-ray radiation, i.e. the wavelength range between 400 nm and 100 nm. The entire UV spectrum is typically divided into 4 areas here, namely UV-A (315 nm-400 nm), UV-B (280 nm-315 nm), UV-C (200 nm-280 nm) and vacuum UV or V-UV (100 nm-200 nm). The germicidal, disinfecting effect of UV radiation is achieved mainly with the wavelength ranges of UV-B and UB-C. The germicidal effect of UV-A is relatively small compared with UV-B and UV-C.

Virtually all water disinfecting systems are operated using UV lamps, which are configured as gas discharge lamps with a mercury content in the gas filling. Mercury produces inter alia a dominant emission curve at 254 nm, which is close to a maximum of the wavelength-dependent effectiveness of UV light for the disinfection of microorganisms. The dependence of effectiveness on the wavelength has a local maximum of 260 nm in most microorganisms, i.e. a specific dose of UV radiation of this wavelength is particularly effective. Initially, the effectiveness drops to 240 nm towards the shorter wavelengths and then increases again. The range between 240 nm and 200 nm with a good level of effectiveness is also suitable for disinfecting microorganisms.

Two types of lamps are used in the main, so-called low pressure lamps which are operated at a gas pressure of less than 0.1 mbar. These low pressure lamps have an extremely narrow-band curve spectrum and in the cited wavelength range almost exclusively emit UV-C radiation with a wavelength of 254 nm. They are characterised by extremely high electrical efficiency, since approximately 40% of the total electrical power consumed is converted into radiated power of the cited wavelength. The disadvantage with low pressure lamps is that the absolute radiated power is relatively low in relation to their overall size and consequently a large number of lamps have to be used in disinfecting systems with a large throughput of water. These systems are correspondingly expensive. Their advantage on the other hand is that the radiation output only has to be monitored at 254 nm to control the lamps, since other components only play a minor part in the disinfection activity and the effective curve can therefore be used directly to control the system.

DE 20 2004 012 686 U1 describes a disinfecting device comprising a UV lamp, which is arranged in a piston and the emission thereof is monitored using a sensor that is not described in further detail. In the event of deviation from a target value, a signal is to be given indicating that cleaning is required.

A disinfecting system comprising UV lamps, which is monitored using two sensors, is known from DE 10 2008 051 239 A1. A deterioration and possible attenuation of the overall radiation output is determined by means of a different geometric arrangement of the sensors, for example, by a different distance or a different angle of detection. The Lambert-Beer'sche law is used here to determine any tarnishing of the lamp casings caused by deposits. This document contains no indication of the spectral sensitivity of the UV sensors. Neither does it state that both the UV sensors may have different spectral sensitivities.

Other water disinfecting systems use so-called medium pressure lamps. The internal pressure of said lamps is between approx. 0.1 and 10 bar. The lamps are operated at higher temperatures and with considerably more compact dimensions have much greater power consumption and correspondingly higher UV radiation output. The higher temperatures and the higher pressure inside the lamp initiate other UV-C curves and continuum radiation between 240 nm and 200 nm. As stated above, this range is also relevant in terms of disinfection performance since the effect of a given UV dose on microorganisms in this wavelength range is also great.

To date, the monitoring of medium pressure sensors has been similar to the monitoring and control of the radiation output of low pressure lamps. UV sensors are used for this purpose that cover part or the whole of the spectrum. The performance of the medium pressure lamp is then controlled such that the total emission registered by the sensor corresponds to requirements and specifications. A spectrum is thus covered in the prior art which is dominated by curves and a continuum with wavelengths of more than 240 nm. An ultraviolet sensor for said monitoring is described in US 2004/0200975 A1, for example. An SiC sensor is disclosed here which has maximum sensitivity at approximately 260 nm.

SUMMARY OF THE INVENTION

It has been shown that the suitability of said monitoring of medium pressure lamps for controlling and monitoring the disinfection performance of UV lamps is limited. The purpose of the present invention is therefore to create a device for monitoring and controlling the radiation output of medium pressure lamps in water disinfecting plants, which can be used to control biologically active UV-C radiation such that a specified disinfection performance is achieved reliably and at the same unnecessarily high consumption of electrical energy can be avoided.

Because the device has a first UV sensor having its maximum sensitivity to UV radiation between 200 and 240 nm, preferably maximum sensitivity between 200 and 230 nm and more preferably a maximum of 220 nm, the biologically particularly effective spectrum range between 200 and 240 nm can be covered using this first UV sensor and minor fluctuations of the emitted intensity in this wavelength range compensated for, which do not vary significantly in overall radiation intensity in the entire UV range and in the UV-C range. Advantageously two sensors are used, wherein a second UV sensor covers the spectral range with wavelengths above 240 nm. In this manner the ratio between the radiation output between 200 nm and 240 nm is compared with the radiation output between 240 nm and 300 nm. This ratio is an indication of the technical state of the lamp, for example in terms of operating conditions and deterioration.

Alternatively, a sensor can also be used, the spectral sensitivity of which can be switched between both cited wavelength ranges. Such a sensor would then include the first UV sensor and the second UV sensor in the form of two separate UV sensitive elements which are integrated into a sensor housing.

Provision can also be made for the use of a resolution sensor in the style of a spectrometer which is used to measure the shortwave portion of the UV-C range between 200 nm and 240 nm. The wavelength range between 200 nm and 240 nm from the resolution spectrum is evaluated and used to control the UV lamp and/or to calculate the actual disinfection performance of the system.

The first UV sensor for the range between 200 nm and 240 nm is preferably a semi-conductor sensor, which is provided with filter means, which let pass the wavelength range between 200 nm and 240 nm and block other wavelengths, in particular the range with wavelengths >240 nm.

Since in the method as per the invention for monitoring and controlling a water disinfecting system having at least one broadband UV emitter arranged in a channel, for example, of a mercury medium pressure lamp type or a excimer lamp, wherein at least a first UV sensor is provided, which is arranged in the water at a distance from the broadband UV emitter, and the first UV sensor is connected to a control unit, which is set up to control the performance of the broadband UV emitter or of the volumetric flow of water through the channel,
- the first UV sensor (103) has a maximum sensitivity between 200 nm and 240 nm,
- a signal from the first UV sensor (103) is evaluated during operation,
- a UV dose in the wavelength range between 200 nm and 240 nm is calculated based on the signal from the first UV sensor (103), and
- the UV dose determined at the site of the first UV sensor (103) is used as a measurement for calculating the disinfection performance of the water disinfecting system,
- the disinfection performance achieved can be determined accurately at any time and adjusted where appropriate.

If further provision is made that a UV spectrum of efficacy for a predefined microorganism is taken as a basis for calculating the disinfection performance, the required inactivation rate for said microorganisms can be measured and adjusted where appropriate if the microbial contamination of the water or wastewater is known.

If, also for the calculation of disinfection performance, the microorganism can be selected from a group, which includes viruses, bacteria and protozoa, a response can be made to various resulting contaminations, for example, when post-treating the discharge from a wastewater treatment plant.

If a second UV sensor with a maximum sensitivity between 240 nm and 300 nm is provided, a measurement can be calculated from the ratio between the signals from the first UV sensor and the second UV sensor, which indicates the deterioration of the broadband UV emitter.

If the electrical efficiency of the broadband UV emitter is controlled ultimately according to the sensor signal, both a changing UV transmission of the water as well as the start of deterioration of the emitter can be counterbalanced.

BRIEF DESCRIPTION OF THE DRAWINGS

An embodiment of the present invention is described in detail below using the drawing. The drawing also shows the general technical background in the form of the UV spectra of various lamps and effect diagrams for the disinfection performance of various wavelengths on different microorganisms.

FIGS. 1, 2 and 4 show drawings from the prior art which are useful in terms of explaining the technical facts.

DETAILED DESCRIPTION OF THE INVENTION

Figure 1:
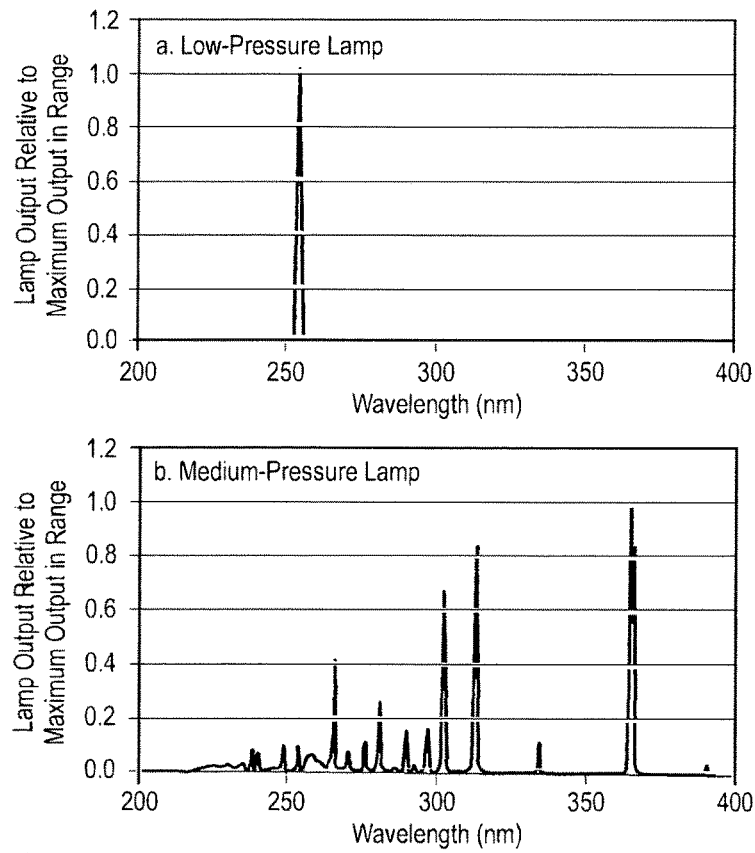
FIG. 1 shows a comparison between the spectrum of a low pressure lamp and the spectrum of a medium pressure lamp (prior art)

FIG. 1 shows two different spectra. The emission curve of a low pressure lamp is shown at 254 nm at the top in FIG. 1. It can be seen immediately that monitoring the UV emission at this wavelength is appropriate in order to control the overall UV radiation output of a low pressure lamp at a specific given value.

FIG. 1 shows at the bottom the spectrum of a medium pressure lamp. A large number of curves between 240 nm and approx. 370 nm can be seen here. Controlling the performance of such a medium pressure lamp solely on the basis of a UV sensor, which has maximum sensitivity at 260 nm, can only control the overall UV radiation output if the relative intensities of the various curves and the underlying continuum do not change.

Figure 2:
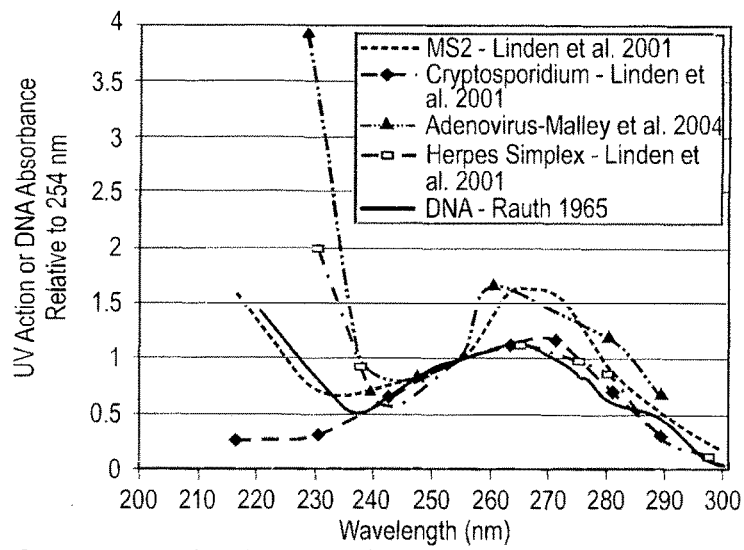
FIG. 2 shows the dependence of the effect of UV rays on different microorganisms on the wavelength (prior art)

It can be seen in practice, however, that firstly the proportion of UV radiation between 200 and 240 nm depends on design of the medium pressure lamp. Modern high-performance lamps emit a significant proportion of their overall radiation output in said shortwave range, whereas older lamps, which are designed and operated differently, only emit a small part of their overall radiation output in said range. FIG. 1 suggests in the lower spectrum that the overall proportion of the UV radiation of a medium pressure lamp in the range between 200 and 240 nm is low compared with the overall emission. However, in terms of biological effectiveness in water disinfecting systems, which are contaminated with microorganisms, it is precisely this wavelength range that is extremely significant. This can be demonstrated with the help of FIG. 2. FIG. 2 shows the effect of UV radiation on the DNA of various microorganisms depending on the wavelength. The different curves shown in FIG. 2 are scaled to a relative effect of 1 at 240 nm. It is noticeable that the effect of UV radiation between 240 and 300 nm on the microorganisms tested is more or less the same (with a fluctuation of perhaps approx. 50%). However, below 240 nm, the effect of the UV radiation on the DNA of the various microorganisms changes dramatically. There are microorganisms, which absorb relatively little UV radiation in the shortwave range and consequently the UV effect on these microorganisms remains relatively slight. However, there are other microorganisms, which show a considerable increase in UV absorption below 240 nm and thus also inactivation as a result of UV radiation.

FIG. 2 therefore shows that the variation in radiation output between 200 and 240 nm can, in the case of some microorganisms, make a huge difference in terms of the disinfection performance of a UV disinfecting system, if the effect of the UV radiation at low wavelengths increases as sharply as demonstrated in the case of some microorganisms in FIG. 2.

There are other influences on the spectrum of UV radiation which is emitted by a medium pressure lamp. The relationship between radiation output between 200 and 240 nm and the overall emission of the lamp is dependent only on the design and operating method of the lamp. If UV light spreads out from the radiation source, the light also interacts with the various materials in the radiation path before it reaches the microorganisms. The materials in the radiation path are firstly the gas filling of the lamp itself, the silica piston of the lamp, the air between the silica piston and a protective covering, a sheath that may be provided between the UV lamp and the water to be treated and finally the water itself. Absorption, reflection, diffraction and diffusion, which affect the spectrum, occur on these materials and their surfaces.

Figure 3:
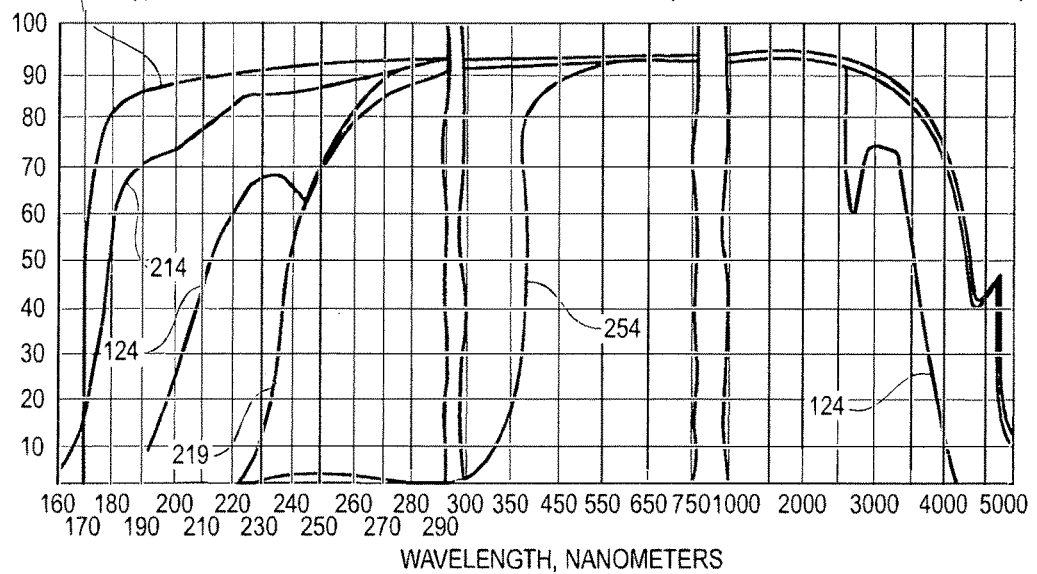
FIG. 3 shows example transmission spectra for various types of fused silica.

FIG. 3 shows, for example, the transmission spectra for UV radiation in various grades of fused silica. In the wavelength range of interest here between 200 and 300 nm, the synthetic fused silica identified as 021 has the best transmission of a sustained approx. 90%, whereas the fused silica identified as 219 shows a clear decrease below 260 nm and below 220 nm is virtually non-transparent to UV radiation. The grade identified as 124 has a minimum transmission at 245 nm and decreases again from 230 nm. At 200 nm, transmission is just 25%. FIG. 3 is intended to show that a medium pressure lamp, which emits a significant proportion of its radiation output between 200 and 240 nm, i.e. in the wavelength range which, according to FIG. 2 is particularly effective for some microorganisms, may lose its radiation output in this range either completely or partially in the event of an unsuitable selection of fused silica for the sheath. The range between 260 and 300 nm is virtually the same for the various silica grades. If the radiation output of the medium pressure lamp is controlled based on a sensor, which is only sensitive between 260 and 300 nm, absorption influences from various types of silica are not taken into account.

Figure 4:
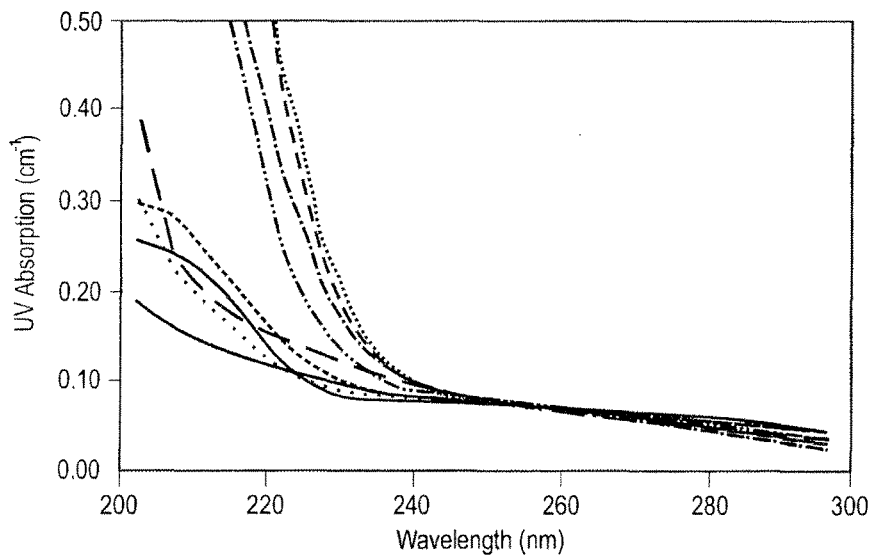
FIG. 4 shows several absorption spectra of water samples in the range between 200 and 300 nm (Prior art from: *USEPA* (2006) *Ultraviolet Disinfection Guidance Manual for the Long Term* 2 *Enhanced Surface Water Treatment Rule, EPA* 815-R-06-007. Office of Water, Washington, D.C.)

FIG. 4 shows various absorption spectra of water samples between 200 and 300 nm. Whereas water samples with very low UV absorption in the shortwave range only show absorption of approx. 20% at 200 nm, water samples with higher UV absorption are specified upwards of a wavelength range of approx. 230 nm with UV absorption of 40% or higher. Absorption at wavelengths of more than 240 nm is substantially the same for all samples. This example also shows that controlling radiation output using sensors, the sensitivity of which is between 260 and 300 nm, cannot take sufficient account of changes in the UV absorption of the treated water. If a UV sensor is used as per the invention to control and monitor the radiation output of the medium pressure lamp, which is sensitive in the range between 200 and 240 nm, the radiation reaching the site of the desired effect can be controlled reliably even if the UV absorption fluctuates.

Figure 5:
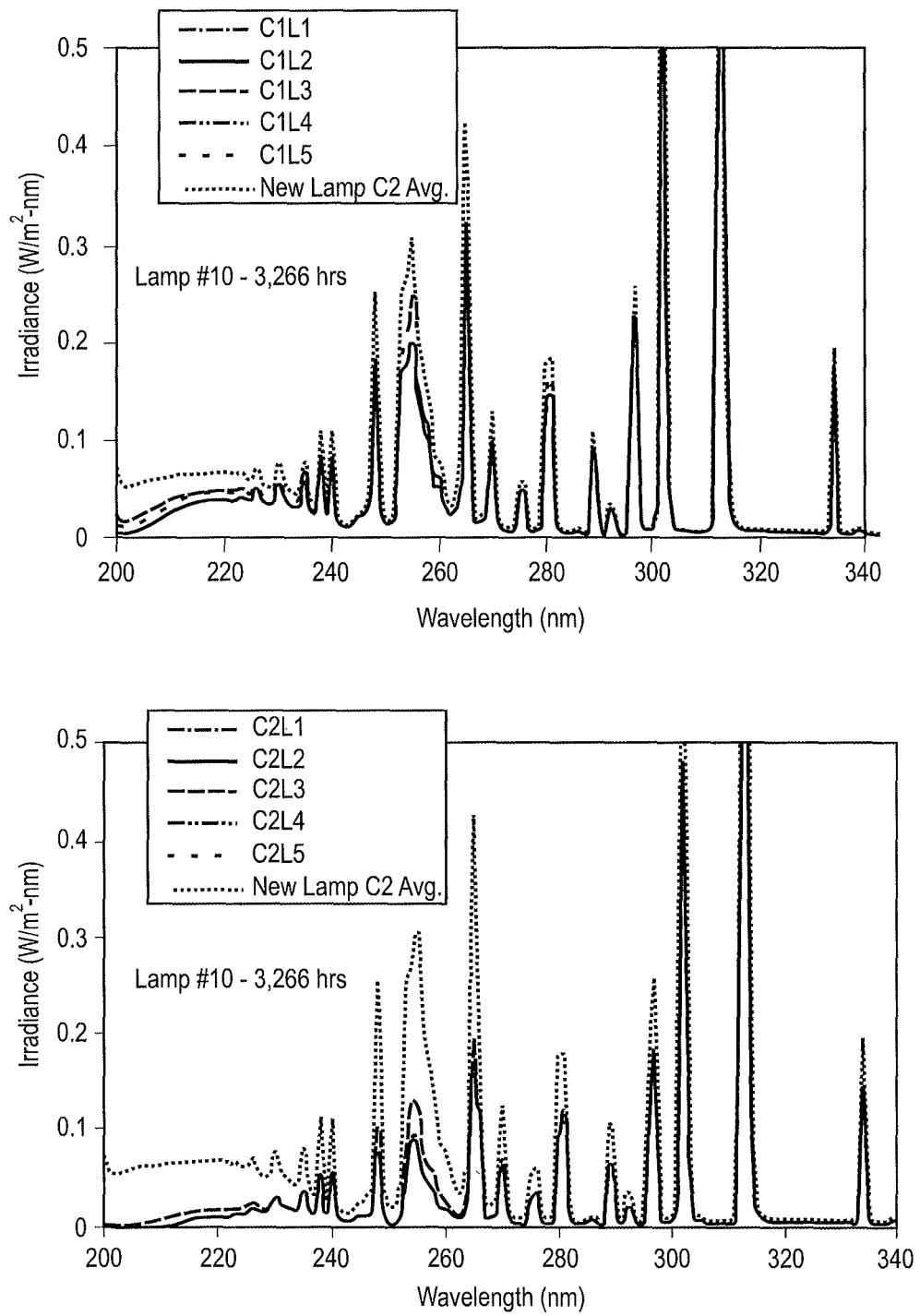
FIG. 5 shows spectra of medium pressure lamps depending on the deterioration of the lamps.

FIG. 5 shows using examples how the spectra of medium pressure lamps change over an operating period of 3,266 hours. The higher emission spectra represent the output of new lamps whilst the curves below these reflect the output of aged lamps. It is clear that the deterioration causes output to be reduced by approx. 50% in the region of 260 nm, however the decline in output between 200 and 240 nm is significantly greater. In the bottom example, the range between 200 and 210 nm has ceased to exist almost completely.

When controlling the disinfecting system according to intensity in the region of 260 nm, it would therefore not be taken into account that the decline in output is significantly greater between 200 and 240 nm. It is therefore advantageous in terms of controlling a UV disinfecting system to control according to radiation output between 200 and 240 nm.

Figure 6:
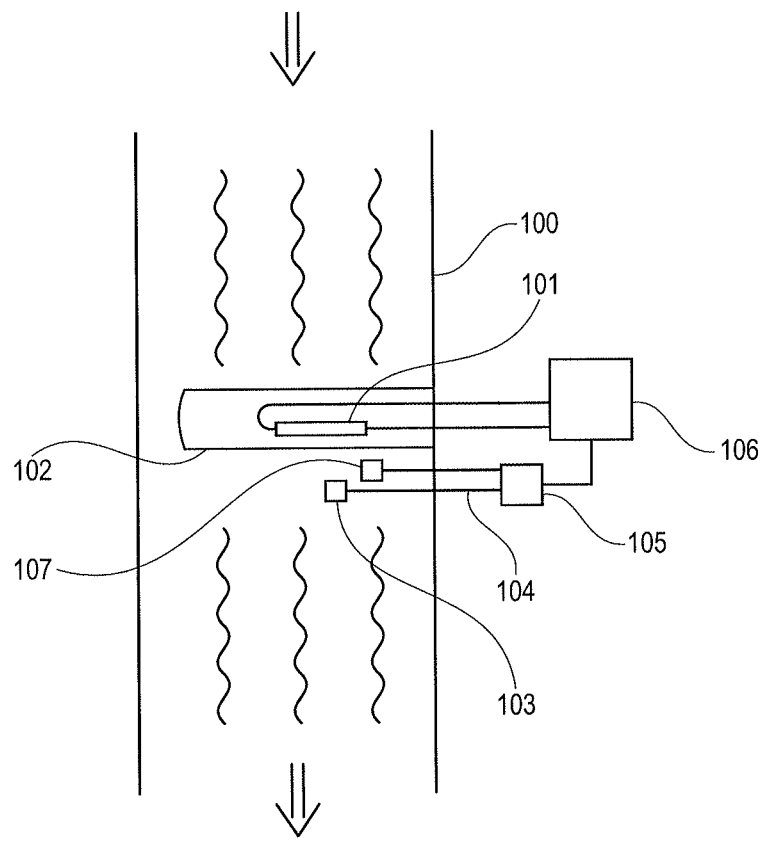
FIG. 6 shows an arrangement as per the invention as a schematic block diagram.

FIG. 6 shows a block diagram of a UV disinfecting system controlled as per the invention.

A channel 100 guides a flow of water (wastewater or drinking water). In the case of wastewater, the channel can be an open or a closed sluice. In the case of drinking water, typically a closed stainless steel channel is provided.

The water flows past a mercury medium pressure lamp 101, which is arranged in a UV transparent sheath 102 and consequently is not in contact with the water.

A first UV sensor 103 is arranged in the water at a distance from the sheath 102, said sensor is sensitive to UV radiation in the wavelength range between 200 and 240 nm. The distance between the first UV sensor 103 and the sheath 102 is selected such that there is a stretch of water between the first UV sensor 103 and the sheath 102, as said stretch of water is also in the middle between the sheath 102 and the microorganisms present in the water. The exact distance is not crucial, since it is more important that as much water lies between in the radiation path between the sheath 102 and the first UV sensor 103 such that a decrease in the UV radiation reaching the first UV sensor 103 can be measured during operation through the UV absorption of the water.

The first UV sensor 103 emits a signal during operation, which is representative of the incoming radiation intensity in the wavelength range between 200 and 240 nm. The signal is emitted via a first signal transmission 104 to a control unit 105. The control unit 105 in turn controls a power supply system 106 such that the lamp 101 produces the intended UV intensity which is necessary for the required disinfection performance.

The first UV sensor 103 is sensitive precisely in the range of the UV-C spectrum in which the disinfection effect depends very heavily on the biological effectiveness and the wavelength, particularly for different microorganisms. The first UV sensor 103 receives the radiation in the cited range emitted by the lamp 101, wherein a change in the output spectrum is taken into account in terms of time, absorption by the sheath and the water, dispersion and other influences.

Output-reducing influences are taken into account which have less impact in the region of 260 nm wavelength.

Optionally, a further sensor can be provided as a second UV sensor 107, which is also provided for measuring the UV radiation in the water, which, however, as in conventional systems for monitoring or controlling broadband UV emitters, has its maximum sensitivity in the longer-wave range, at approx. 260 nm. Said second sensor 107 emits the radiation intensity in the longer-wave range of the UV-C spectrum to the control unit 105, which can then calculate from this the overall radiation output in the UV-C range and in the short-wave portion of the UV-B range, without however taking account of the particularly important short-wave UV-C range, which is covered by the first UV sensor 103. The control unit 105 can reach a conclusion on the condition of the disinfecting system and in particular the lamp 101 from the ratio of intensities, which are measured firstly by the first UV sensor 103 and secondly, by the second UV sensor 107, and can generate an alarm in the event of an excessive decrease in UV output in the wavelength range of the first UV sensor 103.

Figure 7:
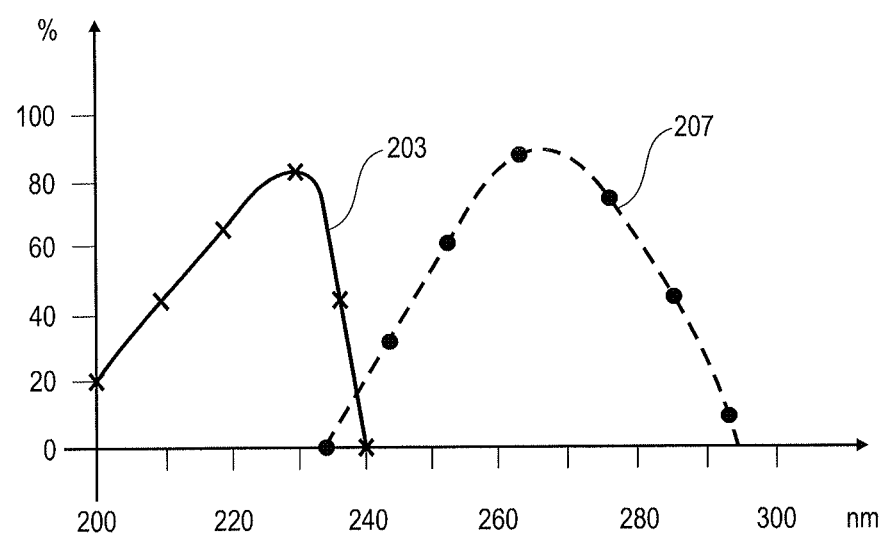
FIG. 7 shows preferred sensitivity curves for the sensors in FIG. 6.

Lastly, FIG. 7 shows a sensitivity spectrum 203 of the first UV sensor 103 and a sensitivity spectrum 207 of the second UV sensor 107. The curve 203 for the first UV sensor 103 has maximum sensitivity at approx. 225 nm whereas there is virtually no sensitivity above 240 nm or below 200 nm. The curve 207 of the second UV sensor 107 has a maximum at 260 nm wherein the spectral sensitivity of the second UV sensor 107 is close to zero below 235 and above 295 nm.

The control system described thus allows precise monitoring and controlling of the disinfecting system in the important wavelength range between 200 nm and 240 nm and consequently precise information is available regarding the inactivation or disinfection performance to be achieved and also in respect of specific microorganisms where appropriate.

The invention claimed is:

1. A device for monitoring and controlling water disinfecting systems having at least one broadband UV emitter arranged in a channel, the at least one broadband UV emitter having an internal pressure of between 0.1 bar and 10 bar and having a deterioration in intensity over time that is greater in a first wavelength range between 200 nm and 240 nm than in a second wavelength range between 240 nm and 300 nm, said device comprising:
   a first UV sensor arranged in the water at a distance from the broadband UV emitter, the first UV sensor having a maximum sensitivity to UV radiation in the first wavelength range;
   a second UV sensor having a maximum sensitivity in the second wavelength range; and
   a control unit connected to the first UV sensor and the second UV sensor, the control unit programmed to control output of the broadband UV emitter based upon measurements from the first UV sensor.

2. The device according to claim 1, wherein the first UV sensor has a maximum sensitivity to UV radiation in a wavelength range between 200 nm and 230 nm.

3. The device according to claim 1, wherein the first UV sensor has a maximum sensitivity to UV radiation at 220 nm.

4. The device according to claim 1, wherein the second UV sensor has a maximum sensitivity to UV radiation at 260 nm.

5. The device according to claim 1, wherein the first UV sensor has a filter that lets pass UV radiation in the range of wavelengths between 200 nm and 240 nm, and blocks wavelengths outside of the range of wavelengths between 200 nm and 240 nm.

6. The device of claim 1, wherein the first UV sensor has essentially no spectral sensitivity above 240 nm or below 200 nm.

7. The device of claim 1, wherein the second UV sensor has a spectral sensitivity close to zero below 235 nm and above 295 nm.

8. The device of claim 1, wherein the device is configured to generate an alarm if a signal corresponding to a ratio of intensities measured by the first UV sensor and the second UV sensor shows a decrease in UV output in the wavelength range of the first UV sensor indicative of a deterioration of the broadband UV emitter.

9. A device for monitoring and controlling water disinfecting systems, the device comprising:
   at least one broadband UV emitter arranged in a channel and having a deterioration in intensity over time that is greater in a first wavelength range between 200 nm and 240 nm than in a second wavelength range between 240 nm and 300 nm;
   at least one first UV sensor arranged in the water at a distance from the broadband UV emitter, wherein the first UV sensor has a maximum spectral sensitivity to UV radiation in the first wavelength range;
   a second UV sensor arranged in the water at a distance from the broadband UV emitter, the second UV sensor having a maximum spectral sensitivity to UV radiation in the second wavelength range, the second UV sensor being located closer to the at least one broadband UV emitter than the at least one first UV sensor; and
   a control unit connected to the first UV sensor and the second UV sensor, wherein the control unit is programmed (a) to control an output of the broadband UV emitter based upon a signal from the first UV sensor, and (b) to generate an alarm if a signal corresponding to a ratio of intensities measured by the first UV sensor and the second UV sensor shows a decrease in UV output in the wavelength range of the first UV sensor indicative of a deterioration of the broadband UV emitter.

10. The device of claim 9, wherein the first UV sensor has essentially no spectral sensitivity above 240 nm or below 200 nm, and the second UV sensor has a spectral sensitivity close to zero below 235 nm and above 295 nm.

11. A device for monitoring and controlling water disinfecting systems having
   at least one broadband UV emitter arranged in a channel and having a deterioration in intensity over time that is greater in a first wavelength range between 200 nm and 240 nm than in a second wavelength range between 240 nm and 300 nm,
   wherein said device has a first UV sensor and a second UV sensor, which are arranged in the water at a distance from the broadband UV emitter, and wherein the first UV sensor and the second UV sensor are connected to a control unit which is programmed to control an output of the broadband UV emitter, wherein the first UV sensor includes a filter that is configured to let pass a wavelength range between 200 nm and 240 nm and block all other wavelengths,
   wherein the first UV sensor has essentially no spectral sensitivity above 240 nm or below 200 nm, and the second UV sensor has a spectral sensitivity close to zero below 235 nm and above 295 nm.

* * * * *